(12) United States Patent
Eldin et al.

(10) Patent No.: US 6,376,728 B1
(45) Date of Patent: Apr. 23, 2002

(54) METHOD, COMPOSITION AND MIXTURE FOR INHIBITING MONOMER POLYMERIZATION

(75) Inventors: Sherif Eldin, Houston; John Link, Humble, both of TX (US)

(73) Assignee: Hercules Incorporated, Wilmington, DE (US)

( * ) Notice: Subject to any disclaimer, the term of this patent is extended or adjusted under 35 U.S.C. 154(b) by 0 days.

(21) Appl. No.: 09/597,155

(22) Filed: Jun. 20, 2000

(51) Int. Cl.$^7$ .................................................. C07C 7/20
(52) U.S. Cl. ............................. 585/5; 585/24; 252/403; 252/404
(58) Field of Search ............................. 585/2, 4, 5, 24; 252/403, 404

(56) References Cited

U.S. PATENT DOCUMENTS

| | | | |
|---|---|---|---|
| 3,674,651 A | | 7/1972 | Otsuki et al. |
| 4,105,506 A | * | 8/1978 | Watson .......................... 208/9 |
| 4,466,905 A | | 8/1984 | Butler et al. |
| 4,774,374 A | | 9/1988 | Abruscato et al. |
| 4,915,873 A | | 4/1990 | Abruscato et al. |
| 4,968,843 A | | 11/1990 | Cottmen |
| 5,396,004 A | | 3/1995 | Arhancet et al. |
| 5,426,257 A | | 6/1995 | Arhancet |
| 5,446,220 A | | 8/1995 | Arhancet |
| 5,470,440 A | | 11/1995 | Arhancet |
| 5,489,718 A | | 2/1996 | Arhancet |
| 5,489,720 A | | 2/1996 | Arhancet |
| 5,510,547 A | | 4/1996 | Arhancet et al. |
| 5,545,786 A | | 8/1996 | Winter et al. |
| 5,562,863 A | | 10/1996 | Arhancet |
| 5,648,573 A | * | 7/1997 | Arhancet et al. ............... 585/5 |
| 5,648,574 A | | 7/1997 | Arhancet et al. |
| 5,773,674 A | * | 6/1998 | Arhancet et al. ............... 585/5 |
| 5,907,071 A | | 5/1999 | Arhancet |
| 5,959,126 A | | 9/1999 | Lohr, Jr. et al. |
| 6,200,461 B1 | * | 3/2001 | Eldrin ................... 208/48 AA |

FOREIGN PATENT DOCUMENTS

| | | |
|---|---|---|
| WO | 95/03263 | 2/1995 |
| WO | 99/20687 | 4/1999 |
| WO | 99/21819 | 5/1999 |
| WO | 99/21826 | 5/1999 |
| WO | 99/21827 | 5/1999 |

OTHER PUBLICATIONS

Raevskii, A.B. et al., UDC 678.762.3:678.048:541.124, pp. 12–13 (1968).
Raevskii, A.B. et al., *Kauch. Rezina 29*, (3), pp. 9–10 (1970).
Kotulák, Ludovít et al., Collection Czechoslovak Chem. Commun. 48, pp. 3384–3395 (1983).
Taimr, L. et al., Polymer Degradation and Stability 8, pp. 23–35 (1984).
Taimir, Luděk et al., Die Angewandte Mackromolekulare Chemie 175, pp. 169–180 (1990).
Ignatz–Hoover, Fred et al., Rubber World, 218, pp. 38–40 (May 1998).

* cited by examiner

*Primary Examiner*—Jacqueline V. Howard
(74) *Attorney, Agent, or Firm*—Greenblum & Bernstein, P.L.C.

(57) ABSTRACT

Method of inhibiting polymerization of alkenyl monomers comprising contacting the alkenyl monomers with:

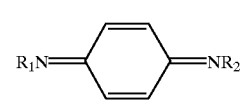

(1)

wherein $R_1$ and $R_2$ independently of one another are alkyl, phenyl, aryl, alkoxy, or carboxy groups; and oxygen.

Mixture comprising:
  a) alkenyl monomers with:

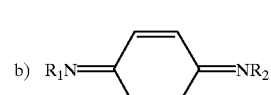

(1)

b)

wherein $R_1$ and $R_2$ independently of one another are alkyl, phenyl, aryl, alkoxy or carboxy groups; and
  c) oxygen.

30 Claims, No Drawings

METHOD, COMPOSITION AND MIXTURE FOR INHIBITING MONOMER POLYMERIZATION

BACKGROUND OF THE INVENTION

1. Field of the Invention

The present invention relates to methods and compositions for inhibiting monomer polymerization, particularly the polymerization of alkenyl monomers, such as vinyl monomers.

2. Background and Material Information

Alkenyl monomers such as styrene undergo polymerization if subjected to heat and/or initiators. Such polymerization presents a problem for manufacturers where the monomer polymerizes during manufacturing and purification processes. Patented technology exists for the use of combinations of oxygen with certain inhibitors to prevent premature polymerization of vinyl monomers during processing.

U.S. Pat. No. 4,466,905 discloses a composition for inhibiting polymerization of vinyl aromatic compounds at higher temperatures which comprises using an effective amount of 2,6-dinitro-p-cresol and an effective amount of a phenylenediamine having the formula:

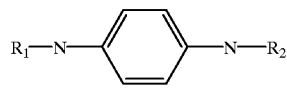

wherein $R_1$ and $R_2$ are alkyl, aryl or hydrogen.

The vinyl aromatic compounds contemplated include styrene, substituted styrene, divinyl benzene, vinyl toluene, vinyl naphthalene and the polyvinylbenzenes. As noted at column 4, line 21, of the patent, oxygen must be added to the system in order for the phenylenediamine co-inhibitor to work properly. Oxygen is added separately into the system to achieve a greater concentration of oxygen in the required area. The oxygen employed may be in the form of oxygen or an oxygen containing gas. Air is listed as a useful and the least expensive source of oxygen, and is preferred for purposes of the patent. The amount of oxygen used depends on the number and spacing of oxygen inlets around the distillation column, and how efficiently oxygen and liquid hydrocarbon are mixed therein. The oxygen flow is increased as long as polymer yields are reduced, limited by the amount of oxygen which would yield an explosive mixture.

U.S. Pat. No. 5,959,126 acknowledges that quinones, such as, for example, the benzoquinones, napthoquinones, anthraquinones, phenanthraquinones, and the like can be prepared by oxidizing the appropriately disubstituted aromatic hydrocarbon derivatives, the substituents being hydroxyl or amino groups in the ortho or para positions. The patent notes that some of the prior art processes utilize a catalytic agent to achieve an acceptable reaction rate, while other processes proceed without catalysts. The patent uses activated carbon catalysts to convert phenylenediamine to quinonediamine in almost quantitive yield.

Kotulak, Ludovit et al., "The Effect of 1,4-phenylenediamine Antidegradants on the Photo-Oxidation of Selected Liquid Hydrocarbons", Institute of Macromolecular Chemistry, Czechoslovak Academy of Sciences, 162 06 Prague 6, *Collection Czechoslovak Chem. Commun.*, Vol 48, pp. 3384–3395 (1983) discusses the antidegradation activity of phenylenediamines and 1,4-benzoquinonediamines. The article states at page 3388 that in the oxidation of both saturated and unsaturated hydrocarbons stabilized with N,N'-disubstituted 1,4-phenyldiamines Ia-If, the corresponding N,N'-disubstituted 1,4-benzoquinonediamines are formed first. Also at page 3388, the article states that "formation of 1,4-benzoquinone diamines II may involve the oxidation with ROO radicals or with oxygen.

U.S. Pat. No. 4,774,374 discloses stabilizing a vinyl aromatic composition with an effective amount of a stabilizer system in which the active member consists essentially of oxygenated species formed by reacting a compound of the formula:

wherein R is $C_6$–$C_{10}$ aryl or $C_7$–$C_{16}$ alkaryl; and $R_1$ is a $C_1$–$C_{12}$ alkyl or $C_3$–$C_{12}$ cycloalkyl, with oxygen. The patent states that the oxygenated species may be formed by reacting oxygen in gaseous form or in the form of an oxygen doner with the phenylenediamine compounds. The patent states that the oxygenated species may be formed in situ by the addition of oxygen to a composition comprising vinyl aromatic compound and the phenylenediamine compound.

U.S. Pat. No. 5,648,573 discloses inhibiting the polymerization of vinyl aromatic monomer by the addition of a composition of a benzoquinone derivative and a hydroxylamine compound, in the presence of oxygen or under oxygen-free processing conditions. The benzoquinone derivatives are represented as:

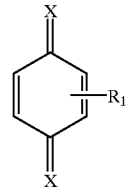

wherein X is N—R or O; R is H, phenyl aryl, nitrogen-containing aryl, or a $C_1$ to $C_7$ alkyl group; and $R_1$ is a $C_1$ to $C_7$ alkyl.

Hydroxylamine compounds useful in the patent have the formula:

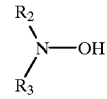

wherein $R_2$ and $R_3$ are the same or different and are hydrogen, akyl, aryl, alkaryl, aralkyl or hydroxalkyl groups.

U.S. Pat. No. 3,674,651 to OTSUKI et al. is said to teach the use of benzoquinone for inhibiting the polymerization of acrylic acid.

Tamir, Luděk et al., "Antioxidants and Stabilizers", 111*, *Die Angewandte Mackromolekulare Chemie*, 175 (1990), pp. 169–180 (No. 2950) discusses the deactivation of alkyls in stabilizing polymers under conditions of relative oxygen deficiency. In this connection, reactions including N,N'-diphenyl-1,4-benzoquinonediimine (IIb) were studied and discussed (p. 170).

Raevskii, A. B. et al., "Inhibition of Oxidation of Isoprene Rubber with Quinone Imines", UDC 678.762.3:678.048:541.124, 1968(?); Raevskii, A. B. et al., "Kauch, Rezina", 1970, 29 (3), pp. 9–10, discloses the inhibition of oxidation of isoprene rubber with quinone imines. N,N-diphenyl-p-quinonediimine was said to inhibit oxidation of SKI-3 rubber. It has been hypothesized that in the inhibition of oxidation of the rubber by the quinonediimine, a high-molecular free radical is formed, whose existence is said to be established by the EPR method.

Taimr, L. et al., "Antioxidants and Stabilizers: Part XCV—A Cooperative Effect Between Antioxidants N-Iso-Proply-N'-Phenyl-1,4-Phenylene Diamine and 2,6-Di-tert-Butylphenol", *Polymer Degradation and Stability* (1984), pp. 23–35 discusses the reactivity of N-iso-propyl-N'-phenyl-1,4-benzoquinonediimine.

Ignatz-Hoover, Fred et al., "6-QD1—A Review of a Multifunctional Chemical for the Rubber Industry", *Rubber World*, May 1988, pp. 38–40, discloses the preparation of quinone diimines by the oxidation of p-phenylene diarnine antidegradants. The listed activities include "antioxidant" for polymers and hydrocarbon liquids.

SUMMARY OF THE INVENTION

The invention seeks to provide an improved method of inhibiting polymerization of alkenyl monomers comprising contacting the alkenyl monomers with:

(1)

wherein $R_1$ and $R_2$ independently of one another are alkyl, phenyl, aryl, alkoxy, or carboxy groups; and oxygen. More specifically, the invention can be directed to polymerization inhibition of vinyl aromatic monomers.

Generally, the ratio of (1) to oxygen is: about 1 to 1000 parts by weight. More preferably, the ratio of (1) to oxygen is about 5 to 500 parts by weight. Most preferably, the ratio of (1) to oxygen is about 10–200 parts by weight.

Generally, the ratio of oxygen and (1) to monomer is about 1 to 2000 per million parts of monomer. Preferably, the ratio of oxygen and (1) to monomer is about 1 to 1000 per million parts of monomer. Most preferably, the ratio of oxygen and (1) to monomer is about 1 to 500 per million parts of monomer.

In one embodiment, $R_1$ and $R_2$ independently of one another are: phenyl, alkyl, aryl or alkoxy. Specific compounds (1) include: one or more of [4-(1,3-dimethyl-butylimino)-cyclohexa-2,5-dienylidene]-phenyl-amine; 3,6-Bis-(phenylimino)-cyclohexa-1,4-diene; 3,6-Bis-sec-butylimino-cyclohexa-1,4-diene; 3,6-Bis-(1,3-dimethyl-butylimino)-cyclohexa-1,4-diene; 3,6-Bis-(1,4-dimethyl-pentylimino)-cyclohexa-1,4-diene; 3,6-Bis-isopropylimino-cyclohexa-1,4-diene; [4-(1,4-dimethyl-pentylimino)-cyclohexa-2,5-dienylidene]-phenyl-amine; (4-isopropylimino-cyclohexa-2,5-dienylidene)-phenyl-amine.

The vinyl aromatic monomers being inhibited may be one or more of: styrene, bromostyrene, divinylbenzene, substituted styrene divinylbenzene, α-methylstyrene, vinyl toluene, vinyl naphthalene and polyvinylbenzene.

The oxygen may be present as pure oxygen, but may alternatively be introduced in the form of air.

An additional inhibitor may be present. In one embodiment, the inhibitor is one or more of nitrophenols, dinitrophenols, quinone methides, and nitroso phenols. In one particular embodiment, the vinyl aromatic monomers are styrene; (1) is [4-(1,3-dimethyl-butylamino)-cyclohexa-2,5-dienylidene]-phenyl-amine; the oxygen is present in the form of air; the ratio of (1) to oxygen is about 1–200 parts by weight; the ratio of oxygen and (1) to styrene is about 1 to 500 per million parts of monomer.

In one particular embodiment, substantially no additional inhibitor is present. In one particular embodiment, hydroxlyarnine having the formula:

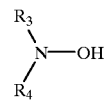

wherein $R_3$ and $R_4$ independently of one another are hydrogen, alkyl, aryl, alkaryl, alkoxy or carboxy groups, is substantially absent.

According to another aspect of the invention, the invention is directed to a mixture comprising:

a) alkenyl monomers;

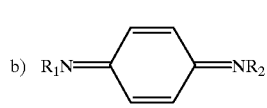

(1)

b)

wherein $R_1$ and $R_2$ independently of one another are alkyl, phenyl, aryl, alkoxy or carboxy groups; and c) oxygen.

Once again, the various ratios, conditions, particular monomers, particular compounds, and the like set forth above with respect to the method, are equally applicable to the mixture, and need not be repeated.

DETAILED DESCRIPTION OF THE INVENTION

The invention relates to methods and compositions and mixtures for inhibiting the polymerization of vinyl aromatic monomer compounds. This is achieved by adding to the monomers a benzoquinone in the presence of oxygen.

The compositions and mixtures of the present invention are effective at inhibiting polymerization of alkenyl monomers such as vinyl aromatic monomers under processing conditions. These processing conditions include but are not limited to preparation, purification, distillation and vacuum distillation processes.

The alkenyl monomers that are treated by the compositions and mixtures of the present invention include, but are not limited to styrene, bromostyrene, substituted styrene divinylbenzene, α-methylstyrene, vinyl toluene, vinyl naphthalene and polyvinylbenzene. The compositions and mixtures of the present invention are particularly effective at inhibiting the polymerization of styrene monomer.

The benzoquinones useful in the present invention generally have the formula:

wherein $R_1$ and $R_2$ independently of one another are alkyl, phenyl, aryl, alkoxy or carboxy groups. These benzoquinones are used in the presence of oxygen to inhibit polymerization. More preferably, $R_1$ and $R_2$, independently of one another are: phenyl, alkyl, aryl or alkoxy. Preferably, the benzoquinone is benzoquinone diimine.

Suggested compositions include:

[4-(1,3-dimethyl-butylimino)-cyclohexa-2,5-dienylidene]-phenyl-amine; 3,6-Bis-(phenylimino)-cyclohexa-1,4-diene; 3,6-Bis-sec-butylimino-cyclohexa-1,4-diene; 3,6-Bis-(1,3-dimethyl-butylimino)-cyclohexa-1,4-diene; 3,6-Bis-(1,4-dimethyl-pentylimino)-cyclohexa-1,4-diene; 3,6-Bis-isopropylimino-cyclohexa-1,4-diene; [4-(1,4-dimethyl-pentylimino)-cyclohexa-2,5-dienylidene]-phenyl-amine; (4-isopropylimino-cyclohexa-2,5-dienylidene)-phenyl-amine.

The most preferred benzoquinonediumine (BQDI) is benzamine, which is [4-(1,3-dimethyl-butylimino)-cyclohexa-2,5-dienylidene]-phenyl-amine and which may be obtained from Flexsys under the tradename Q-Flex QDI and 6-QDI.

Although oxygen is referenced, it is to be understood that the invention is not limited to pure oxygen but rather includes, oxygen in any form including air, and other gaseous forms.

The compounds and mixtures are generally effective at temperatures of 25° C.–200° C., more preferably 50° C.–150° C., and most preferably 80° C.–120° C.

Styrene is typically processed at temperatures between 95° C. and 125° C. The compositions and mixtures of the invention are effective at inhibiting polymerization of styrene over this range of temperatures.

The total amount of benzoquinone derivative and oxygen used in the methods of the present invention is that amount which is sufficient to inhibit polymerization and will vary according the conditions under which the alkenyl monomer is being processed and exposed to high temperatures as well as the manner in which the benzoquinone and oxygen are introduced. At higher processing temperatures and higher monomer concentration, larger amounts of the polymerization inhibiting composition and mixture are generally required.

For purposes of the present invention the term "effective inhibiting amount" is defined as that amount of mixture which is effective in inhibiting polymerization. Preferably, the effective amount of the inventive mixture ranges from about 1 to about 2000 per million parts monomer. More preferably, the effective amount ranges from about 1 to about 1000 per million parts monomer, and most preferably from about 1 to about 500 per million parts monomer. When discussing proportions of the inventive mixture to parts monomer, it is to be understood that it is the total weight of the mixture, which may vary in the proportions indicated below, which is taken into account.

The weight ratio of the benzoquinone to oxygen in the mixture ranges from about 1 to 1000 parts by weight to 1000 to 1 parts by weight, more preferably 5 to 500 parts by weight to 500 to 5 parts by weight, and most preferably from about 10 to 200 parts by weight to 200 to 10 parts by weight. As noted previously, oxygen may be added in the form of air. When so added, it is the amount of oxygen which desirably falls within the stated ranges. It should be noted that systems under consideration often work under vacuum and the invention contemplates adding oxygen to the vacuum which might otherwise exist.

The compositions and mixtures of the present invention can be added to the vinyl monomer by any conventional method at any point along the processing system, either as separate and individual ingredients or as a combination of ingredients. Regardless of how added, the addition of the benzoquinone and oxygen is referred to as a "mixture."

When added in combination, the components of the present invention may be added to the alkenyl monomers as a liquid-gas mixture. Normally, however, the two components are added separately, and in either order. Any solvent that is compatible with the individual ingredients of the composition and the alkenyl monomer may be employed. Examples of solvents include: ethylbenzene and xylene.

As opposed to the prior art, the inventive compositional method can be applied advantageously in the substantial absence of other components. Such components include, but are not limited to hydroxylamines of the formula:

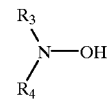

wherein $R_3$ and $R_4$ independently of one another are hydrogen, alkyl, aryl alkyl, or hydroxy alkyl groups.

According to yet another aspect of the invention, the composition of the invention may be added in combination with other inhibitors such as nitrophenols, dinitrophenols, quinone methides, and nitroso phenols.

When so added, the additional inhibitor may be present in any amount sufficient to increase the inhibition by the inventive mixture.

The apparatus utilized to introduce the components, compositions and mixtures of the invention may be conventional nozzles, orifices and the like appropriately positioned to introduce the components, compositions and mixtures into the monomer. Contact between the oxygen and the benzoquinones may be improved by introducing the oxygen into the monomer in a manner which enhances contact between oxygen, benzoquinone and monomer.

EXAMPLES

The invention will now be further described with reference to a number of specific examples which are to be regarded solely as illustrative, and not as restricting the scope of the invention.

Example 1

Vinyl monomer polymerization testing is conducted with styrene obtained commercially from Aldrich. This styrene comes inhibited with TBC. This styrene is passed through inhibitor remover obtained from Aldrich prior to testing. Styrene is refluxed in a oil bath kept at 120° C., under either argon or air (containing the oxygen). Samples from the reaction mixtures are withdrawn every 30 minutes and % polymer in the reaction mixture is obtained by methanol precipitation. Results listed in Table 1 show the difference in % monomer formed in the presence or absence of oxygen. The results demonstrate that in the absence of inhibitor, oxygen (air) accelerates styrene polymerization.

TABLE 1

| Time (min) | % Polymer Blank w/ air | % Polymer Blank w/ Ar |
|---|---|---|
| 0 | 0 | 0 |
| 30 | 4.8 | 2.2 |
| 60 | 15.1 | 4.3 |

Example 2

The presence of benzoquinonediimine (BQDI) with air effectively inhibits styrene polymerization as demonstrated by the results in Table 2. Even though styrene refluxed with air alone shows more polymer than when under an inert Ar atmosphere, the presence of BQDI with air produce significantly less polymer than BQDI alone (under Ar). These results are shown in Table 3.

TABLE 2

| Time (min) | % Polymer BQDI (600 ppm) w/ air | % Polymer BQDI (200 ppm) w/ air |
|---|---|---|
| 0 | 0 | 0 |
| 30 | 0 | 0 |
| 60 | 0 | 0.02 |
| 90 | 0 | 0.04 |
| 120 | 0 | 0.04 |
| 150 | 0 | 0.05 |
| 180 | 0 | 0.06 |
| 210 | 0 | 0.07 |
| 240 | 0 | 0.08 |
| 270 | 0 | 0.19 |
| 300 | 0 | 0.44 |
| 330 | 0.1 | 3.04 |
| 360 | 5.7 | — |

TABLE 3

| Time (min) | % Polymer BQDI (600 ppm) w/ Ar | % Polymer BQDI (200 ppm) w/ Ar |
|---|---|---|
| 0 | 0 | 0 |
| 30 | 0.62 | 0.53 |
| 60 | 2.9 | 2.16 |

Example 4

Crude styrene mixture leaving a dehydroreactor, is cooled, and goes to a storage tank. Inhibitors are typically added either before or after the crude storage tank. From this point, the crude styrene goes to a BT column (benzene toluene). Benzene, toluene and light ends including water are removed overhead in this column with the styrene and ethyl benzene going bottoms. From there flow is to the ethyl benzene splitter (EB/SM splitter) where ethyl benzene is distilled overhead and the heavier styrene goes to the bottom of the column. The majority of polymer is typically formed in the EB/SM splitter. For this reason, air is injected into the reboiler suction line going back into the column. The styrene then goes to the styrene product column where styrene is distilled overhead and heavy polymeric material goes to the bottom of the column. Air, as previously mentioned, is typically injected into the EB/SM column bottoms, however, it can be injected into any other column or reboiler. Inhibitor can be injected into any of the columns or their reboilers, overhead reflux, or condensing systems.

Although the invention has been disclosed with reference to particular means, materials and embodiments, it is to be understood that the invention is not limited to the particulars disclosed and extends to all equivalents within the scope of the claims.

What is claimed is:

1. Method of inhibiting a polymerization of alkenyl monomers consisting essentially of contacting the alkenyl monomers with:

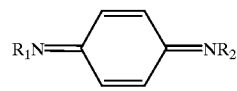

(1)

wherein $R_1$ and $R_2$ independently of one another are alkyl, phenyl, aryl, alkoxy, or carboxy groups; and oxygen.

2. The method as defined by claim 1, wherein the alkenyl monomers are vinyl aromatic monomers.

3. The method as defined by claim 2, wherein the ratio of (1) to oxygen is: about 1 to 1000 parts by weight.

4. The method as defined by claim 3, wherein the ratio of (1) to oxygen is about 5 to 500 parts by weight.

5. The method as defined by claim 4, wherein the ratio of (1) to oxygen is about 10–200 parts by weight.

6. The method as defined by claim 3, wherein the ratio of oxygen and (1) to monomer is about 1 to 2000 per million parts of monomer.

7. The method as defined by claim 3, wherein the ratio of oxygen and (1) to monomer is about 1 to 1000 per million parts of monomer.

8. The method as defined by claim 3, wherein the ratio of oxygen and (1) to monomer is about 1 to 500 per million parts of monomer.

9. The method as defined by claim 2, wherein $R_1$ and $R_2$ independently of one another are: phenyl, alkyl, aryl or alkoxy.

10. The method as defined by claim 9, wherein (1) is one or more of [4-(1,3-dimethyl-butylimino)-cyclohexa-2,5-dienylidene]-phenyl-amine; 3,6-Bis-(phenylimino)-cyclohexa-1,4-diene; 3,6-Bis-sec-butylimino-cyclohexa-1,4-diene; 3,6-Bis-(1,3-dimethyl-butylimino)-cyclohexa-1,4-diene; 3,6-Bis-(1,4-dimethyl-pentylimino)-cyclohexa-1,4-diene; 3,6-Bis-isopropylimino-cyclohexa-1,4-diene; [4-(1,4-dimethyl-pentylimino)-cyclohexa-2,5-dienylidene]-phenyl-amine; (4-isopropylimino-cyclohexa-2,5-dienylidene)-phenyl-amine.

11. The method as defined by claim 10, wherein (1) is [4-(1,3-dimethyl-butylimino)-cyclohexa-2,5-dienylidene]-phenyl-amine.

12. The method as defined by claim 2, wherein said vinyl aromatic monomers are one or more of: styrene, bromostyrene, divinylbenzene, substituted styrene divinylbenzene, α-methylstyrene, vinyl toluene, vinyl naphthalene and polyvinylbenzene.

13. The method as defined by claim 12, wherein said vinyl aromatic monomers are styrene.

14. The method as defined by claim 2, wherein said oxygen is in air.

15. The method as defined by claim 2, wherein said vinyl aromatic monomers are styrene; (1) is [4-(1,3-dimethyl-butylamino)-cyclohexa-2,5-dienylidene]-phenyl-amine; said oxygen is present in the form of air; the ration of (1) to oxygen is about 1–200 parts by weight; the ratio of oxygen and (1) to styrene is about 1 to 500 per million parts of monomer.

16. A mixture consisting essentially of:
a) alkenyl monomers with;

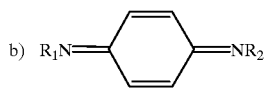
(1)

b) $R_1N=\text{(ring)}=NR_2$ wherein $R_1$ and $R_2$ independently of one another are alkyl, phenyl, aryl, alkoxy, or carboxy groups; and
c) oxygen.

17. The mixture as defined by claim 16, wherein said alkenyl monomers are vinyl aromatic monomers.

18. The mixture as defined by claim 16, wherein the ratio of (1) to oxygen is about 1 to 1000.

19. The mixture as defined by claim 18, wherein the ratio of (1) to oxygen is about 5 to 500.

20. The mixture as defined by claim 19, wherein the ratio of (1) to oxygen is about 10 to 200.

21. The mixture as defined by claim 20, wherein the ratio of oxygen and (1) to monomer is from about 1 to about 2000 per million parts of monomer.

22. The mixture as defined by claim 21, wherein the ratio of oxygen and (1) to monomer is from about 1 to about 1000 per million parts of monomer.

23. The mixture as defined by claim 22, wherein the ratio of oxygen and (1) to monomer is from about 1 to about 500 per million parts of monomer.

24. The mixture as defined by claim 23, wherein $R_1$ and $R_2$ independently of one another are: phenyl, alkyl, aryl or alkoxy.

25. The mixture as defined by claim 24, wherein (1) is one or more of [4-(1,3-dimethyl-butylimino)-cyclohexa-2,5-dienylidene]-phenyl-amine; 3,6-Bis-(phenylimino)-cyclohexa-1,4-diene; 3,6-Bis-sec-butylimino-cyclohexa-1,4-diene; 3,6-Bis-(1,3-dimethyl-butylimino)-cyclohexa-1,4-diene; 3,6-Bis-(1,4-dimethyl-pentylimino)-cyclohexa-1,4-diene; 3,6-Bis-isopropylimino-cyclohexa-1,4-diene; [4-(1,4-dimethyl-pentylimino)-cyclohexa-2,5-dienylidene]-phenyl-amine; (4-isopropylimino-cyclohexa-2,5-dienylidene)-phenyl-amine.

26. The method as defined by claim 25, wherein (1) is [4-(1,3-dimethyl-butylimino)-cyclohexa-2,5-dienylidene]-phenyl-amine.

27. The mixture as defined by claim 17, wherein said alkenyl monomer is one or more of: styrene, bromostyrene, divinylbenzene, substituted styrene divinylbenzene, α-methylstyrene, vinyl toluene, vinyl naphthalene and polyvinylbenzene.

28. The mixture defined by claim 17, wherein said alkenyl monomer is styrene.

29. The mixture as defined by claim 18, wherein said oxygen is in air.

30. The mixture as defined by claim 17, wherein said alkenyl monomers are styrene; (1) is [4-(1,3-dimethyl-butylamino)-cyclohexa-2,5-dienylidene]-phenyl-amine; said oxygen is present in the form of air; the ratio of (1) to oxygen is about 1–200 parts by weight; the ratio of oxygen and (1) to styrene is about 1 to 500 per million parts of monomer.

* * * * *